US012708537B2

(12) United States Patent
Godbey et al.

(10) Patent No.: US 12,708,537 B2
(45) Date of Patent: Aug. 18, 2026

(54) DELIVERY SYSTEM AID AND ASSOCIATED SYSTEMS AND METHODS

(71) Applicant: W. L. Gore & Associates, Inc., Newark, DE (US)

(72) Inventors: Jamin R. Godbey, Flagstaff, AZ (US); Dean A. Shute, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 182 days.

(21) Appl. No.: 16/965,696

(22) PCT Filed: Feb. 6, 2018

(86) PCT No.: PCT/US2018/017037

§ 371 (c)(1),
(2) Date: Jul. 29, 2020

(87) PCT Pub. No.: WO2019/152058

PCT Pub. Date: Aug. 8, 2019

(65) Prior Publication Data

US 2020/0352762 A1 Nov. 12, 2020

(51) Int. Cl.

| | |
|---|---|
| ***A61F 2/962*** | (2013.01) |
| ***A61F 2/01*** | (2006.01) |

(Continued)

(52) U.S. Cl.

CPC .............. *A61F 2/962* (2013.01); *A61F 2/011* (2020.05); *A61F 2/07* (2013.01); *A61F 2/2436* (2013.01);

(Continued)

(58) Field of Classification Search

CPC .. A61F 2/962; A61F 2/011; A61F 2/07; A61F 2/2436; A61F 2/856; A61F 2/954;

(Continued)

(56) References Cited

U.S. PATENT DOCUMENTS

| | | | |
|---|---|---|---|
| 5,653,743 | A | 8/1997 | Martin |
| 6,042,605 | A | 3/2000 | Martin et al. |

(Continued)

FOREIGN PATENT DOCUMENTS

| | | | |
|---|---|---|---|
| CN | 103932820 | A | 7/2014 |
| EP | 1200017 | B1 | 1/2005 |

(Continued)

OTHER PUBLICATIONS

Ballard et al., "Visceral/Renal Artery Debranching for Complex Thoracoabdominal Hybrid Procedures via Retroperitoneal Abdominal Aortic Exposure: A Preliminary Report", Annals of Vascular Surgery, vol. 22, No. 2, 208, pp. 173-178.

(Continued)

*Primary Examiner* — Jing Rui Ou

(57) ABSTRACT

An endoluminal delivery system including an introducer sheath, a delivery catheter configured to pass through the introducer sheath, an endoluminal device releasably maintained along the delivery catheter at a delivery profile, and a guidewire tube removably received by the endoluminal device, the guidewire tube including an enlarged feature configured to prevent insertion of the guidewire tube into a body of a patient.

12 Claims, 12 Drawing Sheets

(51) Int. Cl.
*A61F 2/07* (2013.01)
*A61F 2/24* (2006.01)
*A61F 2/856* (2013.01)
*A61F 2/954* (2013.01)
*A61F 2/06* (2013.01)

(52) U.S. Cl.
CPC .............. *A61F 2/856* (2013.01); *A61F 2/954* (2013.01); *A61F 2002/061* (2013.01); *A61F 2210/0004* (2013.01); *A61F 2210/0014* (2013.01); *A61F 2250/0048* (2013.01)

(58) Field of Classification Search
CPC ........ A61F 2002/061; A61F 2210/0004; A61F 2210/0014; A61F 2250/0048
See application file for complete search history.

(56) References Cited

U.S. PATENT DOCUMENTS

| | | | | |
|---|---|---|---|---|
| 6,352,561 | B1 | 3/2002 | Leopold et al. | |
| 6,361,637 | B2 | 3/2002 | Martin et al. | |
| 6,520,986 | B2 | 2/2003 | Martin et al. | |
| 6,551,350 | B1 | 4/2003 | Thornton et al. | |
| 6,599,316 | B2 | 7/2003 | Vardi et al. | |
| 6,645,242 | B1 | 11/2003 | Quinn | |
| 7,537,606 | B2 | 5/2009 | Hartley et al. | |
| 7,682,380 | B2 | 3/2010 | Thornton et al. | |
| 8,267,988 | B2 | 9/2012 | Hamer et al. | |
| 8,273,115 | B2 | 9/2012 | Hamer et al. | |
| 8,474,120 | B2 | 7/2013 | Hagaman et al. | |
| 8,474,300 | B2 | 7/2013 | Mckinnon et al. | |
| 8,945,200 | B1 | 2/2015 | Eblacas et al. | |
| 9,314,328 | B2 | 4/2016 | Dake et al. | |
| 9,827,118 | B2 | 11/2017 | Hagaman et al. | |
| 12,403,023 | B2 | 9/2025 | Godbey et al. | |
| 2003/0055483 | A1 | 3/2003 | Gumm | |
| 2003/0199967 | A1 | 10/2003 | Hartley et al. | |
| 2004/0098079 | A1* | 5/2004 | Hartley | A61F 2/95 623/1.11 |
| 2004/0098081 | A1* | 5/2004 | Landreville | A61F 2/91 623/1.11 |
| 2004/0133130 | A1 | 7/2004 | Ferry et al. | |
| 2004/0193254 | A1 | 9/2004 | Greenberg et al. | |
| 2004/0199073 | A1 | 10/2004 | Ma | |
| 2004/0230287 | A1* | 11/2004 | Hartley | A61F 2/954 606/108 |
| 2006/0041303 | A1 | 2/2006 | Israel | |
| 2007/0083215 | A1* | 4/2007 | Hamer | A61F 2/954 606/108 |
| 2007/0162109 | A1 | 7/2007 | Davila et al. | |
| 2007/0250154 | A1 | 10/2007 | Greenberg et al. | |
| 2008/0097386 | A1 | 4/2008 | Osypka | |
| 2008/0140110 | A1 | 6/2008 | Spence | |
| 2008/0269866 | A1* | 10/2008 | Hamer | A61F 2/07 623/1.11 |
| 2011/0054586 | A1 | 3/2011 | Mayberry et al. | |
| 2011/0054587 | A1 | 3/2011 | Mayberry et al. | |
| 2011/0270385 | A1 | 11/2011 | Muzslay | |
| 2012/0046728 | A1 | 2/2012 | Huser et al. | |
| 2012/0130472 | A1 | 5/2012 | Shaw | |
| 2012/0290068 | A1 | 11/2012 | Roeder et al. | |
| 2013/0046371 | A1 | 2/2013 | Greenberg et al. | |
| 2013/0103134 | A1 | 4/2013 | Minion | |
| 2013/0103135 | A1 | 4/2013 | Vinluan | |
| 2013/0144373 | A1 | 6/2013 | Shahriari | |
| 2013/0289701 | A1 | 10/2013 | Coghlan et al. | |
| 2014/0180394 | A1 | 6/2014 | Greenberg et al. | |
| 2014/0257464 | A1 | 9/2014 | Roeder | |
| 2014/0316514 | A1 | 10/2014 | Zukowski | |
| 2014/0324150 | A1 | 10/2014 | Stephens et al. | |
| 2015/0306805 | A1 | 10/2015 | Dando et al. | |
| 2016/0143759 | A1 | 5/2016 | Bohn et al. | |
| 2016/0193032 | A1 | 7/2016 | Dake et al. | |
| 2017/0135806 | A1 | 5/2017 | Ombrellaro | |
| 2018/0071076 | A1 | 3/2018 | Guo et al. | |
| 2018/0098837 | A1 | 4/2018 | Shahriari | |
| 2018/0126095 | A1* | 5/2018 | von Oepen | A61M 25/0028 |
| 2018/0153677 | A1 | 6/2018 | Perkins et al. | |
| 2022/0133463 | A1 | 5/2022 | Korte | |
| 2023/0390091 | A1 | 12/2023 | Godbey et al. | |

FOREIGN PATENT DOCUMENTS

| | | | |
|---|---|---|---|
| EP | 1808149 | A1 | 7/2007 |
| JP | 2010-524629 | A | 7/2010 |
| JP | 2012-525227 | A | 10/2012 |
| JP | 2014-500752 | A | 1/2014 |
| WO | 01/08599 | A1 | 2/2001 |
| WO | 2008/133802 | A1 | 11/2008 |
| WO | 2010/104666 | A1 | 9/2010 |
| WO | 2010/127040 | A1 | 11/2010 |
| WO | 2014/145012 | A2 | 9/2014 |

OTHER PUBLICATIONS

Boddepalli et al., "Common Iliac Artery to Renal Artery Bypass Using a Saphenous Vein Graft—An Alternative to Auto Transplantation", CIBTech Journal of Surgery, vol. 6 No. 3, 2017, pp. 1-4.

Gawenda et al., "Hybrid-procedures for the Treatment of Thoracoabdominal Aortic Aneurysms and Dissections", Eur. J. Vasc. Endovasc. Surg., vol. 33, 2007, pp. 71-77.

Greenberg et al., "Beyond the aortic bifurcation: Branched endovascular grafts for thoracoabdominal and aortoiliac aneurysms", Journal of Vascular Surgery, May 2006, pp. 879-886.

International Search Report and Written Opinion received for PCT Patent Application No. PCT/US2018/017037, mailed on Oct. 31, 2018, 13 pages.

International Search Report and Written Opinion received for PCT Patent Application No. PCT/US2020/019916, mailed on Jun. 12, 2020, 12 pages.

Soltesz et al., "Endovascular Repair of Thoracoabdominal Aortic Aneurysms with Fenestrated-Branched Stent-Grafts", Operative Techniques in Thoracic and Cardiovascular Surgery, 2010, pp. 86-99.

Yang et al., "Complex Endovascular Peri-Renal Aortic Aneurysm Repair Preserving Perfusion to a Horseshoe Kidney", 37th Annaul Meeting, Jan. 23-26, 2013, 2 pages.

International Preliminary Report on Patentability received for PCT Patent Application No. PCT/US2020/019916, mailed on Sep. 10, 2021, 9 pages.

Definition of "along", https//www.dictionary.com/browse/along, obtained Dec. 12, 2024.

* cited by examiner

DELIVERY SYSTEM AID AND ASSOCIATED SYSTEMS AND METHODS

CROSS-REFERENCE TO RELATED APPLICATION

This application is a U.S. 371 Application of International Application PCT/US2018/017037, filed Feb. 6, 2018, which claims the benefit of U.S. Provisional Application No. 62/625,654, filed Feb. 2, 2018, both of which are herein incorporated by reference in their entirety.

FIELD

The present disclosure relates generally to endoluminal delivery systems. More specifically the disclosure relates to endoluminal delivery system aids, and even more specifically, removable guidewire tubes of endoluminal delivery systems.

BACKGROUND

Stents are examples of expandable endoluminal prosthetic devices, which may be used to maintain, open or dilate stenotic lesions in body lumens or to repair an aneurysm or dissection. Vascular disease may occur at a branch or bifurcation in a vessel, such as the aortic bifurcation, common iliac arteries, or other such areas. However, placement and deployment of these prosthetic devices at bifurcations can often be problematic.

One technique is to initially deploy across an aneurysm a main body prosthetic device having one or more sidewall openings. The one or more sidewall openings can be aligned with one or more side branch ostia. One or more additional, prosthetic devices can then be deployed through the main body prosthetic device sidewall opening(s) and into the side branch vessel(s). Procedural complications can be encountered while practicing such techniques, including limitations on accurate placement of the main body prosthetic device (e.g., including alignment of sidewall opening(s) to side branch vessel(s)).

Placement of side branch guidewires through the main body prosthetic device, through the sidewall opening(s) and then into the side branch vessel(s) subsequent to main body prosthetic device deployment can be problematic. For example, difficulties can be encountered if the sidewall opening(s) are not properly aligned to begin with, and accessing and passing through the sidewall opening(s) can prove challenging. Additionally, delivery systems that include multiple catheters or other features for maintaining side branch guidewire(s) can be overly complex, and may interfere or complicate removal of the main body delivery catheter prior to the delivery of the side branch prosthetic device(s) through the sidewall opening(s) in the main body prosthetic device.

Alternate procedures that place sidewall opening guidewires prior to the main body device deployment can help with aligning guidewire(s) and/or the sidewall opening(s) with the side branch ostium(s), for example. Some methods and systems have been proposed that include pre-loaded side branch opening guidewires (i.e., guidewires that have been loaded into the side branch opening(s) prior to placing the main body prosthetic device at the desired treatment site) utilize guidewire tubes to assist with pre-loading or otherwise guiding guidewires into the side branch opening(s). U.S. Pat. No. 8,267,988, entitled "Side branched endoluminal prostheses and methods of delivery thereof," issued to Hamer et al., provides some examples of known guidewire tubes and pre-loaded side branch guidewires used for such purposes.

For example, Hamer et al. describe a main body prosthetic device having one or more side branch guidewire lumens, or guidewire tubes, that pass through, or cannulate, the main body prosthetic device and side openings in the main body prosthetic device. One or more guidewires are able to be placed into the main body prosthetic device, and through the side opening(s) by passing the guidewire(s) through the side branch guidewire lumen(s). In some examples, the side branch guidewire lumens are removed prior to advancing the main body device to a desired treatment site in the body. In one method of delivery, as the main body device is advanced, the side opening(s) are self-guided (e.g., by the side branch guidewire(s)) and self-align to the side branch vessel ostium(s). In such examples, the main body device can then be deployed, leaving the side branch guidewire(s) in place. One or more side branch devices can then be advanced along the side branch guidewire(s) through the main body device, through the side wall opening(s) and into the native side branch vessel(s).

SUMMARY

Various examples relate to an endoluminal delivery system including an introducer sheath, a delivery catheter, a first guidewire, an endoluminal device (e.g., a stent, a stent-graft, a vascular filter, a transcatheter valve, or other endoprosthesis), a second guidewire, and a guidewire tube. The guidewire tube includes an enlarged feature and is configured to be removably received by a portion of the endoluminal device.

According to one example ("Example 1"), an endoluminal delivery system includes an introducer sheath having a proximal end, a distal end, a lumen extending between the proximal end and the distal end, and a proximal opening at the proximal end providing access to the lumen. The endoluminal delivery system also includes a delivery catheter configured to be passed through the proximal opening into the lumen of the introducer sheath. The endoluminal delivery system also includes an endoluminal device releasably maintained along the delivery catheter at a delivery profile. The delivery profile is configured so that the endoluminal device can be passed through the proximal opening into the lumen of the introducer sheath while the endoluminal device is maintained in the delivery profile. The endoluminal device has an inner lumen, a first opening providing access to the inner lumen, and a second opening providing access to the inner lumen. The endoluminal delivery system also includes a guidewire tube removably received by the endoluminal device so that the guidewire tube is removable from the endoluminal device when the endoluminal device is in the delivery profile. The guidewire tube passes through the first opening, into the lumen, and out of the second opening of the endoluminal device. The guidewire tube has a first end, a second end, and a lumen configured to receive a guidewire. The guidewire tube also includes an enlarged feature configured to selectively prevent insertion of the guidewire tube through the proximal opening and into the lumen of the introducer sheath.

According to another example ("Example 2") further to Example 1, the proximal opening into the lumen of the introducer sheath is defined by a hemostatic valve.

According to another example ("Example 3") further to any of Examples 1 and 2, the endoluminal delivery system also includes a guidewire received in the lumen of the guidewire tube.

According to another example ("Example 4") further to any of Examples 1 to 3, the endoluminal delivery system also includes a constraint releasably maintaining the endoluminal device in the delivery configuration.

According to another example ("Example 5") further to any of Examples 1 to 4, the enlarged feature includes a portion of the guidewire tube that defines an enlarged outer profile relative to a remaining portion of the guidewire tube.

According to another example ("Example 6") further to any of Examples 1 to 5, the enlarged feature includes at least one of a bead, a ring, a barb, a knob, and a catch.

According to another example ("Example 7") further to any of Examples 1 to 6, the enlarged feature is substantially teardrop shaped.

According to another example ("Example 8") further to any of Examples 1 to 7, the enlarged feature is positioned at a proximal end of the guidewire tube.

According to another example ("Example 9") further to any of Examples 1 to 8, the enlarged feature is positioned at a distal portion of the guidewire tube.

According to another example ("Example 10") further to any of Examples 1 to 9, the enlarged feature defines a maximum diametric dimension that is greater than a maximum diametric dimension of adjacent portions of the guidewire tube by at least 10%, 20%, 30%, 40%, 50%, 60, 100%, 200%, 300%, or more.

According to another example ("Example 11"), an endoluminal delivery system includes an introducer sheath having a proximal end, a distal end, and a lumen extending between the proximal end and the distal end. The endoluminal delivery system also includes a delivery catheter. The endoluminal delivery system also includes a constraint having proximal end, a distal end, a wall extending from the proximal end to the distal end to form a lumen, and at least one opening in the wall. The endoluminal delivery system also includes a guidewire tube having a first end, a second end, and a lumen. The guidewire tube extends from the at least one opening through the lumen of the constraint. The guidewire tube has an increased profile section configured to prevent insertion of the guidewire tube into the introducer sheath.

According to another example ("Example 12"), a method for using an endoluminal delivery system of any of Examples 1 to 10 includes delivering a guidewire to a desired treatment site within the body of a patient. The method also includes inserting the guidewire through the guidewire tube so that the guidewire extends through a lumen of the guidewire tube. The method also includes removing the guidewire tube from the endoluminal delivery system. The method also includes inserting the endoluminal delivery system into the body of a patient and delivery the endoluminal device to the desired treatment site within the body of the patient.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1A:
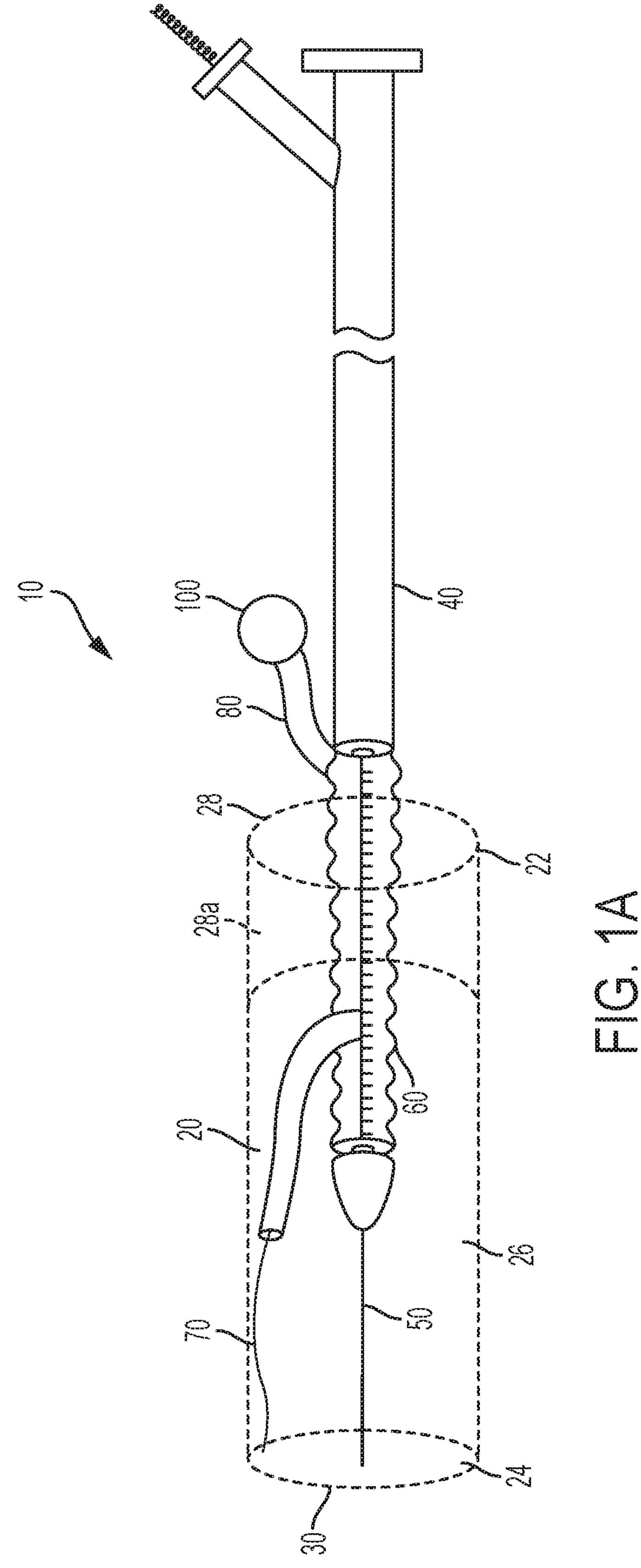
FIGS. 1A and 1B show an endoluminal delivery system, according to some embodiments.

FIG. 1A shows a schematic view of an endoluminal delivery system 10, according to some embodiments. As shown, the endoluminal delivery system 10 includes an introducer sheath 20, a delivery catheter 40, a first guidewire 50, an endoluminal device 60, a second guidewire 70, and a guidewire tube 80. In various examples, the endoluminal device 60 is maintained on the delivery catheter 40 in a delivery configuration for endoluminal delivery, including passage of the endoluminal device 60 through the introducer sheath 20. For reference, a delivery configuration is meant to refer to a diametrically compacted, or simply compacted profile whereas a deployed configuration is meant to refer to a diametrically enlarged, or simply enlarged profile. As described in further detail, the guidewire tube 80 includes an enlarged feature 100 and is configured to be removably received by a portion of the endoluminal device 60 (e.g., prior to delivering the endoluminal device 60 to a desired location in the body of a patient). For reference, the enlarged feature 100 is optionally configured as a stop, a removal aid, an identifier, or combinations thereof.

In various examples, the endoluminal delivery system 10 facilitates deployment of the endoluminal device 60, which may include a stent, a graft, a stent-graft, a vascular filter, a transcatheter valve, or other endoprosthesis, at a desired treatment location within the body of a patient. In some examples, the desired treatment location may be an area of vascular bifurcation such as the aortic arch branches (arteries of the head, arms, and hands), lower branches of the aorta (celiac), renals, mesenterics, iliacs, the femoral, and/or the lower extremities (legs and feet).

As shown in FIG. 1A, the introducer sheath 20 has a proximal end 22, a distal end 24, and a lumen 26 extending between the proximal end 22 and the distal end 24. The introducer sheath 20 may have an inner diameter and a length that depend on the desired treatment location. For example, the inner diameter (e.g., at proximal opening 28) may be between about 3 mm and about 10 mm, and the length may be between about 10 mm and about 30 cm, between about 30 cm and about 70 cm, or alternatively may be over 70 cm.

In some embodiments, the introducer sheath 20 may be substantially straight, tapered, stepped, or any combination thereof. For example, the introducer sheath 20 can have an inner diameter (e.g., defined at proximal opening 28) that is substantially constant along the length of the lumen 26 (e.g., from the proximal end 22 to the distal end 24). In another example, the inner diameter can vary along the length of the lumen 26. For example, the inner diameter may be smaller at the proximal end 22 and increase to a larger diameter at the distal end 24, or vice versa.

In some embodiments, proximal opening 28 at the proximal end 22 provides access to the lumen 26. There may also be a distal opening 30 at the distal end 24 such that, in some embodiments, the delivery catheter 40 can be inserted into the introducer sheath 20 through the proximal opening 28 and exit through the distal opening 30 of the introducer sheath 20.

Figure 1B:
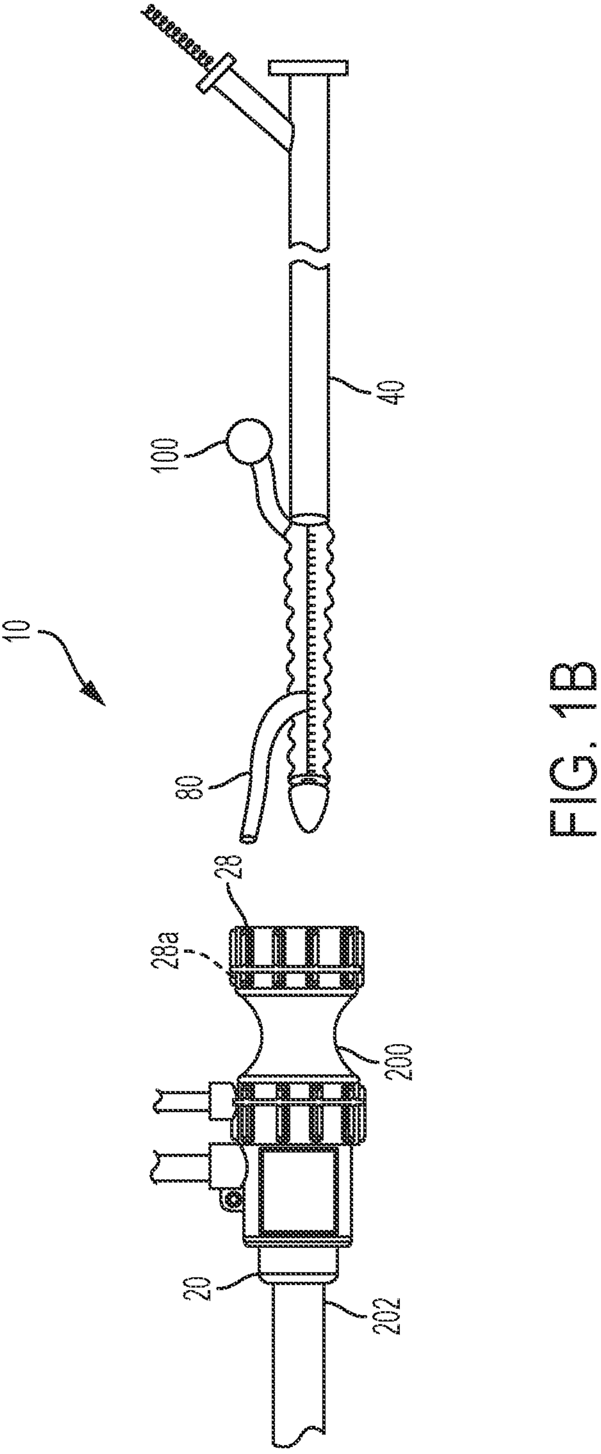

As indicated generally in FIG. 1A, the introducer sheath 20 has a proximal portion 28*a* defined by one or more features of the introducer sheath 20, which, in turn, defines the proximal opening 28 of the introducer sheath 20. In some examples, the proximal portion 28*a* may be tubular projection (e.g., of sheath material), a hemostatic valve that defines the proximal opening 28, or other feature of the introducer sheath 20, such as a luer fitting. Though the proximal portion 28*a* is indicated generally in FIG. 1A by broken lines, and may include a variety of features associated with introducer sheath designs, one specific example of an introducer sheath including a hemostatic valve for the proximal portion 28*a* is that sold under the trade name, "DrySeal Flex Introducer Sheath," available from W.L. Gore & Associates Inc. For example, FIG. 1B provides an example of the introducer sheath 20 with a valve portion 200 defining the proximal portion 28*a* of the introducer sheath 20, including the proximal opening 28, as well as a sheath portion 202 extending from the valve portion 200. From the more schematic representation of FIG. 1A and the associated description, it should be apparent that an introducer sheath having a proximal portion 28*a* formed by another feature (e.g., a luer fitting) and defining the proximal opening 28 is also contemplated.

Figure 2:
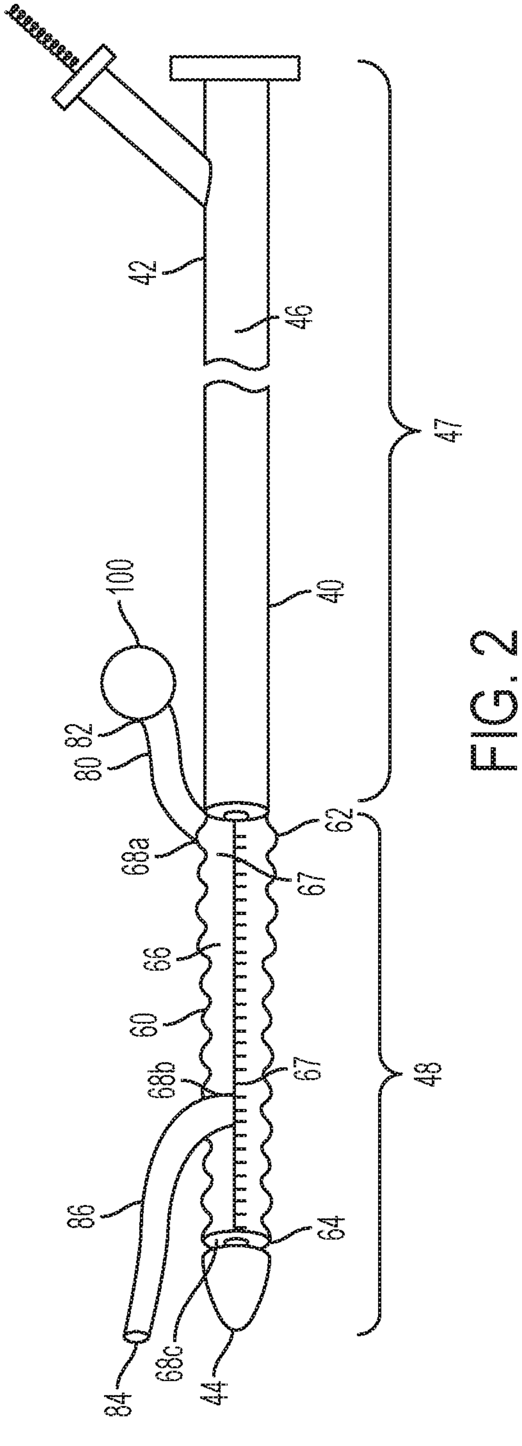
FIG. 2 shows a delivery catheter with an endoluminal device maintained along the delivery catheter, and a guidewire tube, according to some embodiments.

As seen in FIG. 2, the delivery catheter 40 has a proximal end 42, a distal end 44, and an inner lumen 46. As discussed above, the delivery catheter 40 is configured to be passed through the proximal opening 28 and into the lumen 26 of the introducer sheath 20. Thus, the delivery catheter 40 should be sized such that it can be passed through the lumen 26 of the introducer sheath 20. For example, the delivery catheter 40 can have a diameter ranging from about 1 mm to 20 mm, 2 mm to 15 mm, or 2 mm to 6 mm at a portion of the delivery catheter 40 configured to pass through the introducer sheath 20. Although some examples are provided, any variety of diameters is completed.

In some embodiments, the delivery catheter 40 has a proximal portion 47 extending between the proximal end 42 and a point located longitudinally between the proximal end 42 and the distal end 44. The delivery catheter 40 may also have a distal portion 48 extending between the distal end 44 and a point located longitudinally between the proximal end 42 and the distal end 44. Both the proximal portion 47 and the distal portion 48 can have diameters similar to those listed above for the delivery catheter 40.

The delivery catheter 40 generally has a length commensurate with delivering an endoluminal device to a desired treatment site. Thus, the delivery catheter 40 can have a length suitable to deliver any of a variety of prosthetic devices. The length of the delivery catheter 40, including both the proximal portion 47 and distal portion 48, can vary from about 20 cm to over 100 cm depending on the desired treatment location.

Similar to the introducer sheath 20 discussed above, in some embodiments, the delivery catheter 40 may be substantially straight, tapered, stepped, or any combination thereof. For example, the delivery catheter 40 can have a diameter that is substantially constant along the length of the inner lumen 46 (e.g., from the proximal end 42 to the distal end 44). In another example, the inner diameter can vary along the length of the inner lumen 46. For example, the diameter may be smaller at the proximal end 42 and may increase to a larger diameter at the distal end 44, or vice versa.

The delivery catheter 40 can comprise conventional medical grade materials such as nylon, polyacrylamide, polycarbonate, polyethylene, polyformaldehyde, polymethylacrylate, polypropylene, polytetrafluoroethylene, polytrifluorochlorethylene, polyvinylchloride, polyurethane, elastomeric organosilicon polymers, Pebax® polyether block amide, and metals such as stainless steels and nitinol.

In some embodiments, the endoluminal device 60, also referred to herein as an implantable device or simply a device, is mounted on the delivery catheter 40, and specifically by the distal portion 48. In one embodiment, the device 60 is maintained at a delivery diameter such that the device 60 can be passed through the lumen 26 of the introducer sheath 20 and moved to the desired treatment location.

The device 60 has a proximal end 62, a distal end 64, and an inner lumen 66. The device 60 may also include a plurality of openings 67 (three are shown in FIG. 2, though any number is contemplated) providing access to the inner lumen 66. In some examples, the device 60 includes a first opening 68*a* (e.g., an end opening or a side opening) providing access to the inner lumen 66 and a second opening 68*b* (e.g., an end opening or a side opening) providing access to the inner lumen 66, and a third opening 68*c* (e.g., an end opening or a side opening) providing access to the inner lumen 66. Any of the first opening 68*a*, the second opening 68*b*, and/or the third opening 68*c* may be sized to fit the guidewire tube 80 therethrough.

As shown, the first opening 68*a* is an end opening located at the proximal end 62 (FIG. 2). However, the first opening 68*a* may be located at any point between the proximal end 62 and the distal end 64 of the device 60, including proximate the proximal end 62 of the device 60, proximate the distal end 64 of the device 60, or intermediate the proximal end 62 and the distal end 64 of the device 60. In one example, the second opening is located at a point proximate the distal end 64 of the device 60 (FIG. 2). However, the second opening 68*b* is optionally located at any point between the proximal end 62 and the distal end 64 of the device 60, including proximate the proximal end 62 of the device 60, intermediate the proximal end 62 and the distal end 64 of the device 60, or at an end of the device 60. In some embodiments, the device 60 may have more or fewer than three openings. For example, the device 60 can have a first opening 68*a*, a second opening 68*b*, and any number of subsequent openings. The number of openings in any particular embodiment may depend on a variety of factors, including the desired treatment location, the number of access openings desired into the inner lumen (e.g., to receive a desired number of branch devices), or other additional or alternative considerations.

In some embodiments, the device 60 is a stent, a graft, a combination thereof, or another type of prosthetic device altogether. As is generally understood, stents can be used alone or in combination with graft materials. Stents can be configured on the external or internal surface of a graft or may be incorporated into the internal wall structure of a graft. Grafts can have various configurations and can be fabricated, for example, from tubes, sheets or films formed into tubular shapes, woven or knitted fibers or ribbons or combinations thereof. Graft materials can include conventional medical grade materials such as nylon, polyester, polyethylene, polypropylene, polytetrafluoroethylene, polyurethane and elastomeric organosilicon polymers.

In some embodiments, the stent, graft, or other prosthetic device can be either self-expanding or balloon expandable. Typically, a self-expanding device will include at least one shape memory material, such as nitinol. Suitable stent materials include, in addition to nitinol, for example, metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

In some embodiments, the guidewire tube 80 (FIG. 3) has a first end 82, a second end 84, and a lumen 86, a proximal portion 87, and a distal portion 88. The first end 82 and the second end 84 may be open to provide access to the lumen 86 and receive a guidewire therethrough. In some embodiments, only one of the first end 82 or the second end 84 may be open such that the other, opposite end is closed to permit access to the lumen 86 with a guidewire, but not to allow the guidewire to pass all the way through the lumen 86.

As referenced above, the guidewire tube 80 is generally sized, shaped, and otherwise configured to fit a guidewire therethrough. In some embodiments, the guidewire tube 80 can have an inner diameter ranging from about 0.1 mm to about 2 mm, 0.2 mm to about 1.5 mm, or 0.3 mm to about 1 mm, or any range including any of the foregoing ranges. The guidewire tube may have a wall thickness ranging from about 0.05 mm to about 1 mm, 0.06 mm to about 0.5 mm, or 0.08 mm to about 0.3 mm, or any range including any of the foregoing ranges. In some embodiments, the wall thickness may be substantially uniform along a length of the guidewire tube 80. For example, the wall thickness may be substantially the same from the first end 82 to the second end 84. In other embodiments, the wall thickness may be non-uniform along the length of the guidewire tube 80 such that the wall thickness varies between the first end 82 and the second end 84.

The length of the guidewire tube 80 can vary depending on the desired treatment location. For example, the length of the guidewire tube 80 may be tailored for a particular prosthetic device. In some embodiments, the guidewire tube 80 may be significantly shorter than the overall catheter length and may be slightly longer than the device 60. For example, the guidewire tube 80 may have a length ranging from about 1 cm to about 30 cm, 2 cm to about 20 cm, or 4 cm to about 15 cm, or any range including any of the foregoing ranges.

The guidewire tube 80 can comprise suitable medical grade materials similar to those described above for the delivery catheter 40. Examples of such materials include conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, polyether ether ketone (PEEK), elastomeric organosilicon polymers, and metals such as stainless steel and nitinol. In some embodiments, the material may be sufficiently translucent so that a guidewire can be visualized by the practitioner as the guidewire is advanced through the guidewire tube 80.

In some embodiments, one or more additional guidewire tubes similar to the guidewire tube 80 may be used. Additional guidewire tubes (not shown) may be useful, for example, when treating a bifurcated area within the body of a patient (or an area with multiple branch ostia) using an endoprosthesis with multiple sidewall openings.

Figure 3:
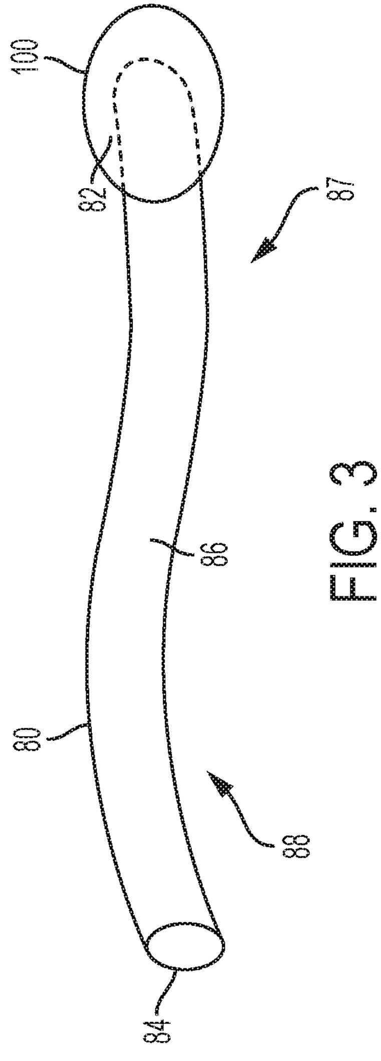
FIG. 3 shows a guidewire tube including an enlarged feature, according to some embodiments.
Figure 4B:
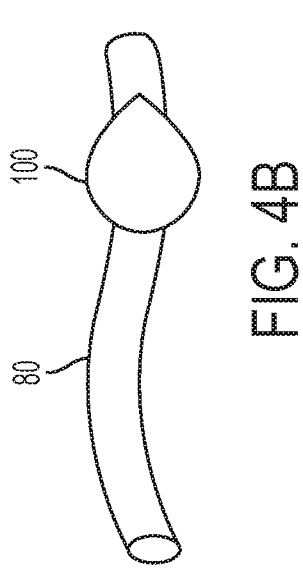
FIGS. 4*a-d* shows additional features of a guidewire tube including an enlarged feature, according to some embodiments.
Figure 4D:
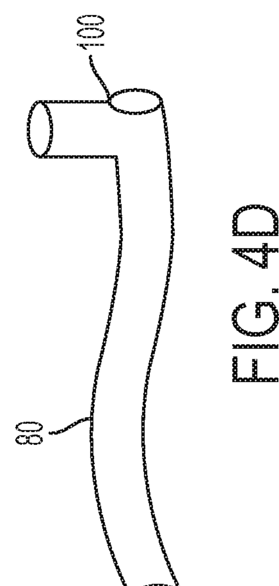
Figure 4A:
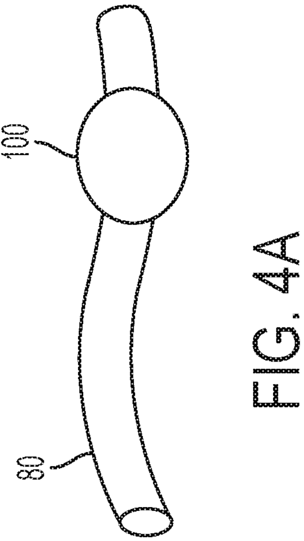
Figure 4C:
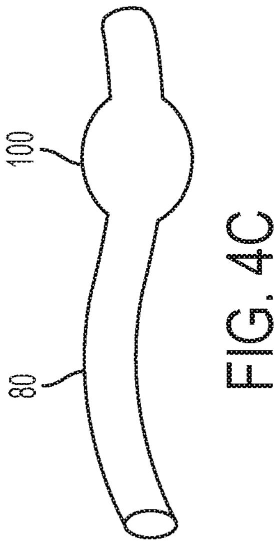

In some embodiments, the guidewire tube 80 includes an enlarged feature 100 (FIG. 3). The enlarged feature 100, also referred to as a removal aid, an identifier, or any combination thereof, may serve as a visual reminder to the practitioner to remove the guidewire tube 80 prior to insertion of the device 60 and/or delivery catheter 40 into the introducer sheath 20. The enlarged feature 100 may also aid in removal of the guidewire tube 80 by providing an enlarged profile for the practitioner to grip when pulling, sliding, or otherwise removing the guidewire tube 80. In yet another embodiment, the enlarged feature 100 may prevent removal of the guidewire tube 80 from the device 60 and/or delivery catheter 40 in one direction, while enabling removal in the opposite direction. In some examples, the enlarged feature 100 is a diametrically enlarged portion of the guidewire tube 80. For example, the enlarged feature optionally defines a maximum diametric dimension that is greater than that of adjacent portions of the guidewire tube 80 by at least 10%, 20%, 30%, 40%, 50%, 60% 100%, 200%, 300%, or any range including any of the foregoing ranges. Although some examples have been provided, any enlarged profile portion of any desirable dimension is contemplated.

In some embodiments, the enlarged feature 100 is located at the first end 82 of the guidewire tube 80 (FIG. 3). However, the enlarged feature 100 may be optionally located at the second end 84 of the guidewire tube 80, along the proximal portion 87, along the distal portion 88, or along any other point along the guidewire tube 80 between the first end 82 and the second end 84.

FIGS. **4*a-d* show example alternative configurations of the guidewire tube 80 and the enlarged feature 100. As shown, the enlarged feature 100 may be any one of a bead, a ring, a crimp, a bulge, a barb, a knob, a foot, a catch, or any other feature that provides an enlarged outer profile to prevent insertion of the device 60 and/or delivery catheter 40 into the introducer sheath 20 prior to removal of the guidewire tube 80. For example, in one embodiment, the enlarged feature 100 has a diameter that is larger than the diameter of the guidewire tube 80. In other embodiments, the enlarged feature 100 may have a different shape, color, or profile than the guidewire tube 80. For example, the enlarged feature 100 may be substantially round, teardrop-shaped, L-shaped, hook-shaped, or any other shape that prevents insertion of the guidewire tube 80 into the introducer sheath 20**.

In some examples, multiple guidewire tubes are provided (e.g., as part of a single delivery system, surgical kit, or other arrangement), where each of the multiple guidewire tubes includes an enlarged feature, such as the enlarged feature 100. In such instances, differing enlarged features configurations may be used (e.g., different size, shape, color, or other differentiator) to differentiate between multiple guidewires, guidewire tubes, or various other features.

In some embodiments, the enlarged feature 100 comprises the same material as the guidewire tube 80. However, the enlarged feature 100 may also comprise a different material than the guidewire tube 80. For example, the enlarged feature 100 may comprise ultra-violet (UV) curable adhesives and sealants, thermoset plastics, thermoplastics, compliant polymers, extrusions such as bump extrusions, metal ferrules, and various overmolded components.

The surface of the enlarged feature 100 may vary depending on various factors, including desired use and/or practitioner preference. In some embodiments, the enlarged feature 100 is substantially smooth. However, in other examples, the surface may comprise indentations, lines, dimples, crosshatches, or any other such texture or combination of textures.

Referring to FIG. 2, the device 60 is coupled to the delivery catheter 40 at the distal portion 48 of the delivery catheter 40. In some examples, the guidewire tube 80 is removably received through the first opening 68*a* of the device 60. However, the guidewire tube 80 can also be received by the second opening 68*b*, the third opening 68*c*, or any other additional opening in the device 60. In some embodiments, the guidewire tube 80 may enter through one opening and exit through another opening.

Any additional guidewire tubes necessary for completion of the desired procedure may extend, for example, from the first opening 68*a* to the second opening 68*b*, the third opening 68*c*, or other, additional openings within the device 60.

In another optional configuration (FIG. 5), the guidewire tube 80 may be removably received by one or more portions of the delivery catheter 40. For example, the guidewire tube 80 may enter through the proximal end 42 or the distal end 44 of the delivery catheter 40. In some embodiments, the guidewire tube 80 may enter through the proximal end 42 or the distal end 44 and exit through a first opening 49 in the delivery catheter 40. However, it is contemplated that the guidewire tube 80 may enter and exit through any combination of openings in the delivery catheter 40. Similarly as discussed above, any number of additional guidewire tubes necessary for completion of the desired procedure are contemplated.

Figure 5:
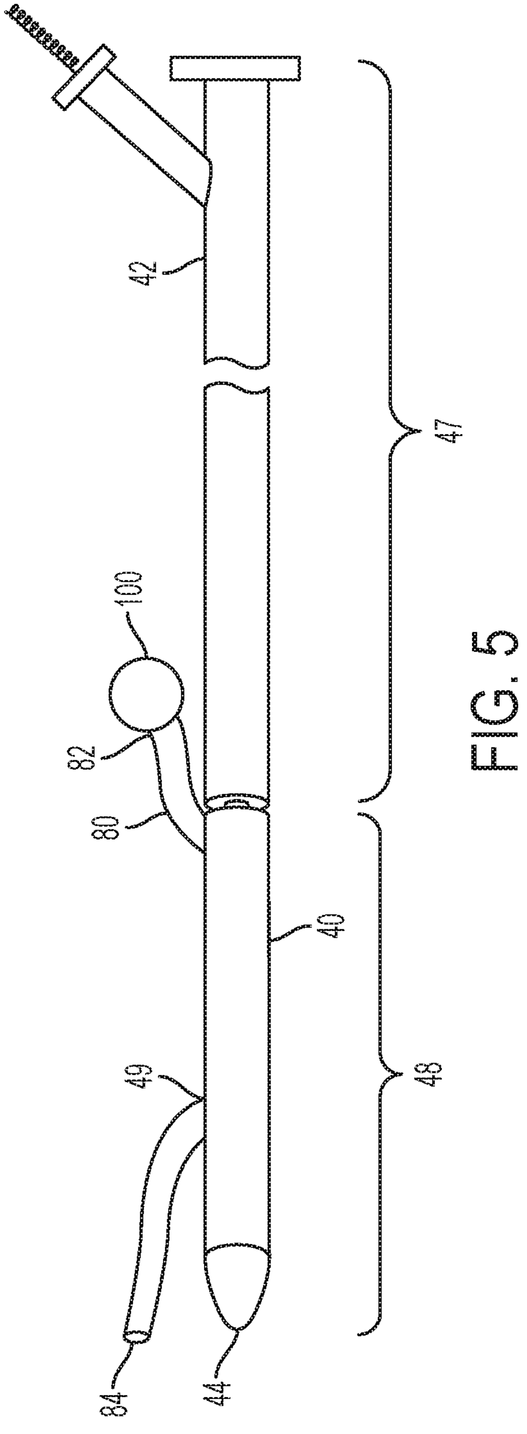
FIG. 5 is a schematic view of a delivery catheter having a guidewire tube therethrough, according to some embodiments.

In FIG. 5, the enlarged feature 100 is shown at the first end 82 of the guidewire tube 80. However, as discussed above, the enlarged feature 100 can be located at the first end 82, the second end 84, or at any other point between the first end 82 and the second end 84.

In some embodiments, the enlarged feature 100 is adhesively attached to the guidewire tube 80. The enlarged feature 100 must be attached sufficiently to withstand a removal force (i.e. pulling, sliding, etc.). For example, the enlarged feature 100 should be adequately adhered/attached/connected to the guidewire tube 80 so as not to deform, move from its original position, or detach from the guidewire tube 80 during removal of the guidewire tube 80 from the device 60. Therefore, in various embodiments, the enlarged feature 100 may have an attachment force of at least about 1 lbf, at least about 4 lbf, at least about 7 lbf, or at least about 10 lbf. In other embodiments, the attachment force is between about 1 to 12 lbf, between about 6 to 12 lbf, and/or between about 8 to 12 lbf, or any range including any of the foregoing ranges.

Figure 6:
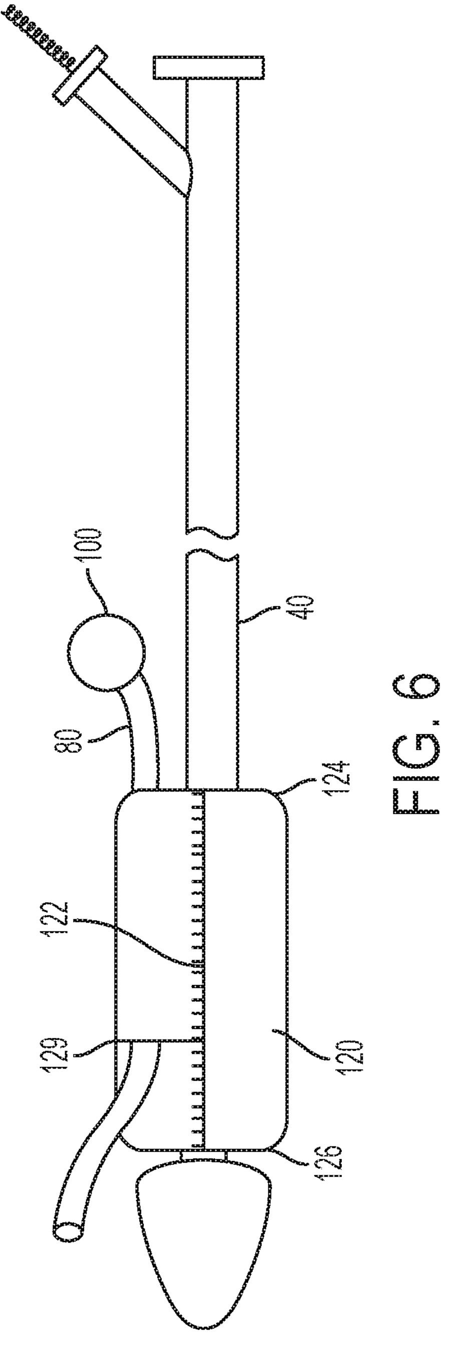
FIG. 6 is a schematic view of a delivery catheter with an endoluminal device maintained along the delivery catheter and a constraint, according to some embodiments.

In FIG. 6, the device 60 is shown in a compressed state (e.g., at a delivery profile) at the distal portion 48 of the delivery catheter 40. In one embodiment, the device 60 is maintained in the compressed state by a constraint 120.

The constraint 120 includes a proximal end 124, a distal end 126, and a lumen 129. In some embodiments, the constraint 120 is a sleeve, a sheath, or a cover capable of compressing the device 60 to the appropriate delivery profile, also referred to herein as the delivery diameter. For example, the device 60 may be compressed to a delivery diameter ranging from about 3 mm to 13 mm or up to about 110 mm, or any range including any of the foregoing ranges, or other value as desired.

The constraint 120 may be disposed over all or a portion of the device 60. In some embodiments, the constraint 120 is laced together by a deployment cord 122, which may form a generally longitudinal seam along the constraint 120.

In some embodiments, the constraint 120 includes a first opening 129 oriented perpendicular to the longitudinal seam. The first opening 129 may provide an exit point for the guidewire tube 80 to exit the delivery catheter 40 and constraint 120. However, in other embodiments, the constraint 120 may not include a first opening 129. For example, the guidewire tube 80 may exit through a stitch line of the longitudinal seam. Details relating to constraining sheath materials, sheath methods of manufacture and main body compression techniques can be found in, for example, U.S. Pat. No. 6,352,561 to Leopold et al., and U.S. Pat. No. 6,551,350 to Thornton et al.

Figure 7:
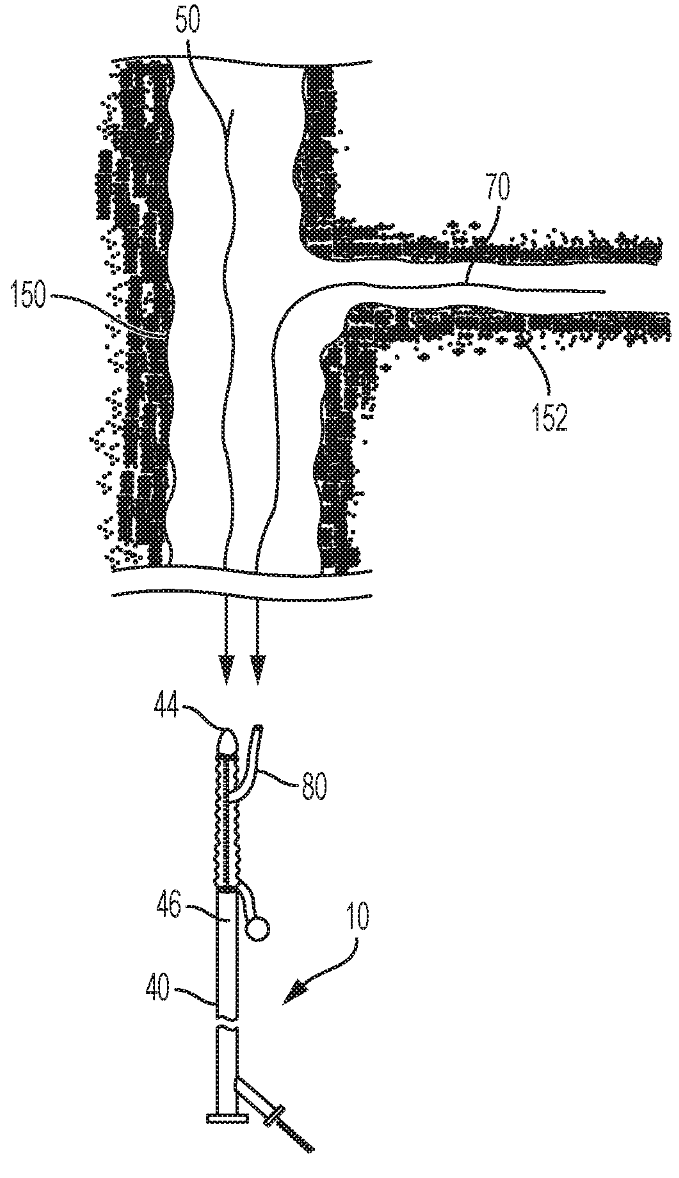
FIGS. 7-11 show a method for using an endoluminal delivery system, according to some embodiments.

FIGS. 7-11 show a method of using the endoluminal delivery system 10. As shown in FIG. 7, the first guidewire 50 is passed through the introducer sheath 20 (not shown) and placed into a main body lumen 150 and the second guidewire 70 is placed into a branch lumen 152. The first guidewire 50 is then threaded proximally through the distal end 44 and into the inner lumen 46 of the delivery catheter 40. The second guidewire 70 is threaded into the removable guidewire tube 80. Typical guidewire diameters include, for example, 0.089 cm (0.035 inches) and 0.36 cm (0.014 inches). However, it should be understood that other size guidewires can be used depending on the particular procedure, desired treatment location, and/or the practitioner's preferences.

Figure 8:
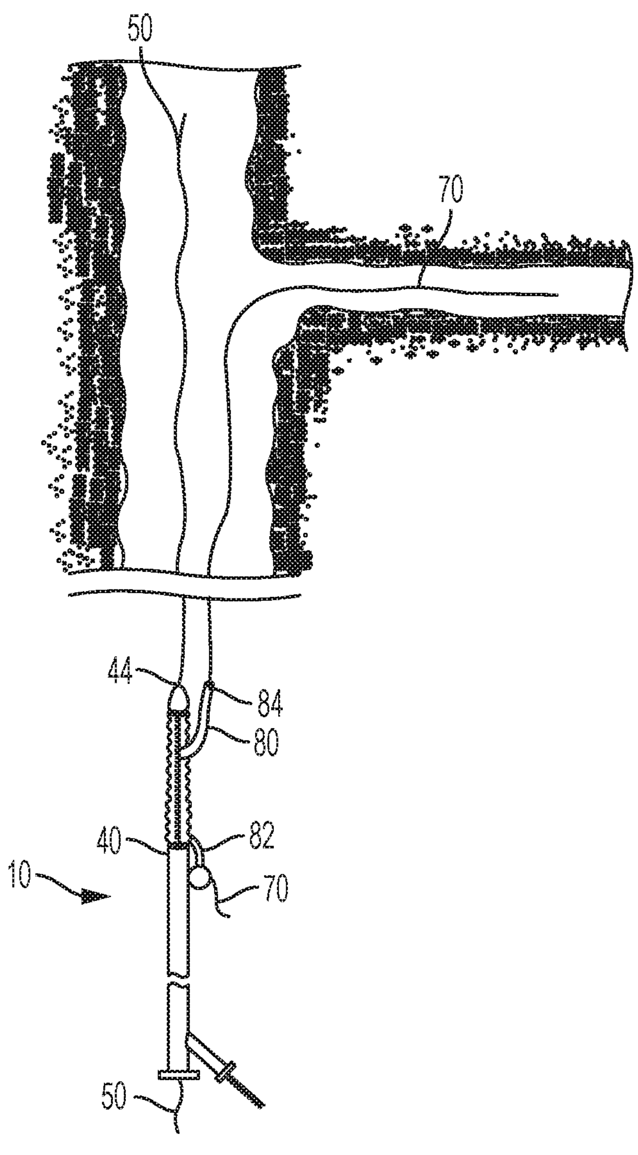

FIG. 8 shows the first guidewire 50 and the second guidewire 70 threaded through the delivery catheter 40 and the guidewire tube 80, respectively. In FIG. 8, both the first end 82 and the second end 84 of the guidewire tube 80 are open such that the second guidewire 70 extends out of both ends. However, in other embodiments, the first end 82 of the guidewire tube 80 may be closed such that it provides a stopping point for the second guidewire 70 such that the second guidewire 70 does not extend out of the first end 82.

Figure 9:
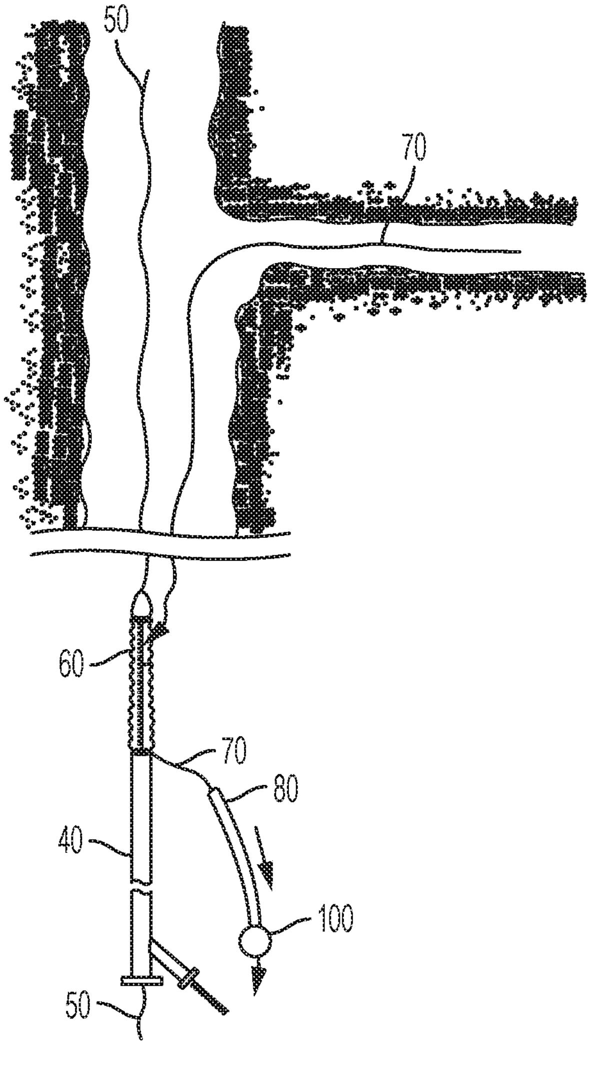

Once the second guidewire 70 is placed within the guidewire tube 80, the guidewire tube 80 can be removed from the device 60 proximally in a direction shown by the arrows in FIG. 9. In another configuration, the guidewire tube 80 may be removed distally in the opposite direction of the arrows. As discussed above, the enlarged feature 100 may aid in removal of the guidewire tube 80 by providing an enlarged portion or handhold for the practitioner to grip. The enlarged feature 100 may also provide a visual reminder to the practitioner to remove the guidewire tube 80 prior to insertion of the delivery catheter 40 and device 60 into the body of the patient. Further, the enlarged feature 100 may facilitate removal in only one direction (i.e., either proximally in the direction denoted by the arrows in FIG. 9 or distally in the opposite direction of the arrows in FIG. 9).

Figure 10:
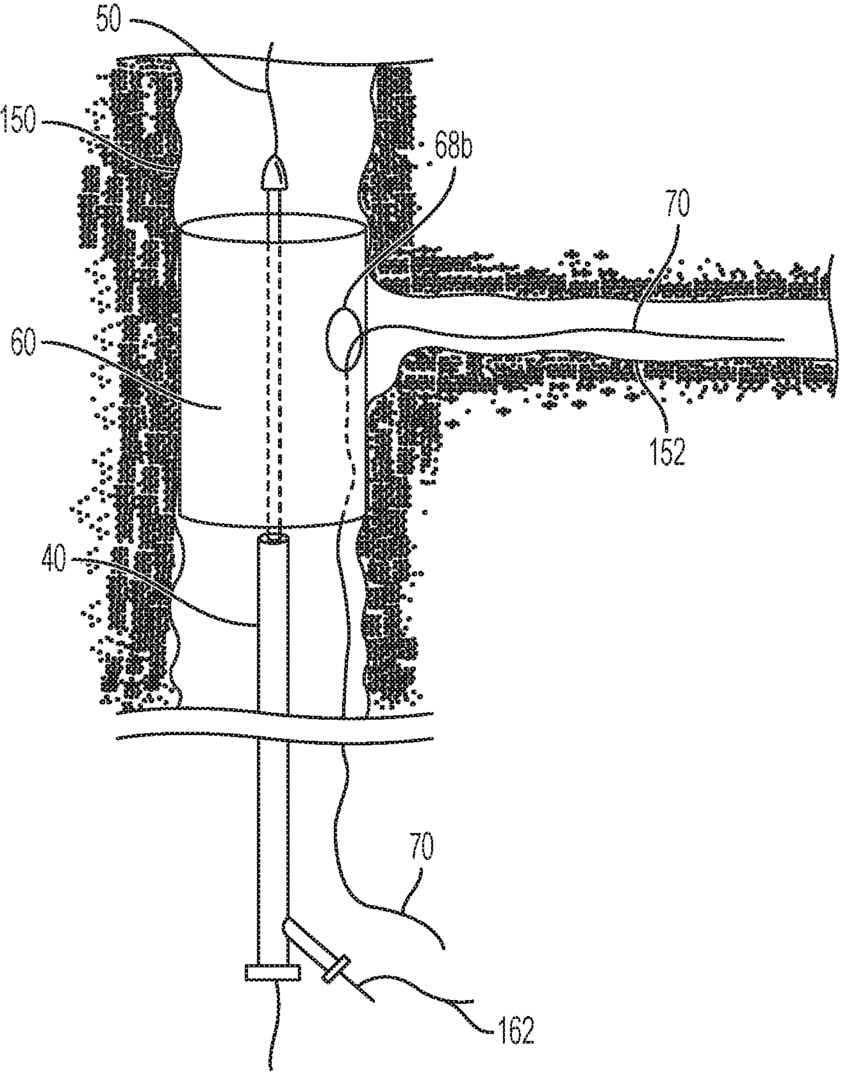

Once the guidewire tube 80 is removed, the delivery catheter 40 with device 60 maintained at the distal portion 48 is advanced along the first guidewire 50 to the desired treatment location until the second opening 68*b* is aligned with the branch lumen 152. FIG. 10 shows deployment of the device 60 within the main lumen 150. As shown, the second opening 68*b* is aligned with the branch lumen 152 and the second guidewire 70 remains extended through the second opening 68*b* and the branch lumen 152.

Figure 11:
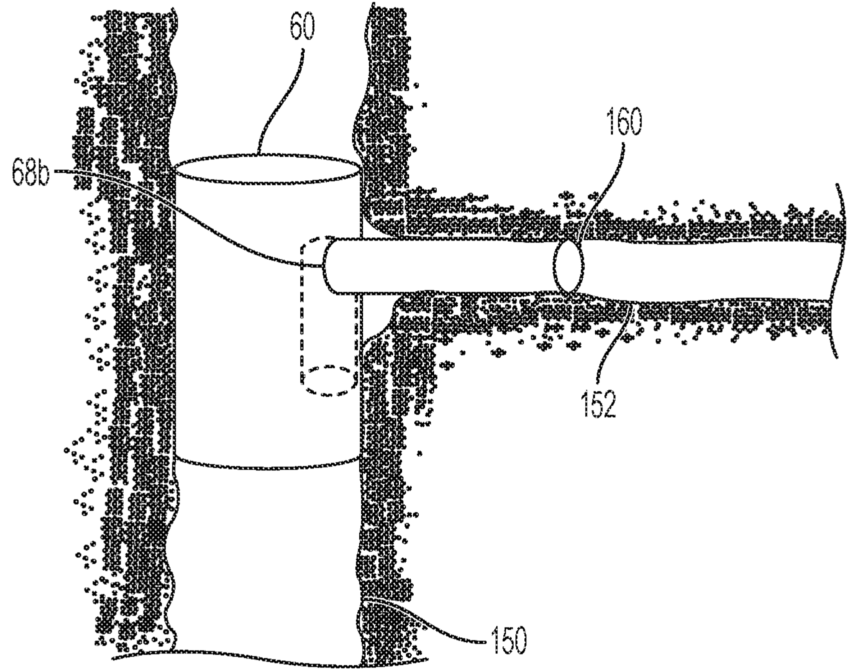

After deployment of the device 60 within the main lumen 150, a branch device 160 (FIG. 11) may be advanced along the second guidewire 70 to the branch lumen 152. In some embodiments, the branch device 160 can be a stent, graft, or other prosthetic device similar to the device 60. The branch device 160 can be compressed in a delivery profile and can include a constraint similar to the device 60, as discussed above. Further, the branch device 160 can include a branch deployment cord 162 (FIG. 10), which can be released once the branch device 160 is in the desired location within the branch lumen 152. In some embodiments, the branch device 160 may be self-expandable or balloon expandable. In some examples (e.g., self-expandable branch device examples), when the branch deployment cord 162 is pulled, the branch device 160 expands to fit the branch lumen 152, as shown in FIG. 11.

As discussed above, the endoluminal delivery system 10 may include any number of openings, guidewire tubes, guidewires, and/or branch devices for the desired application. This may depend, for example, on the desired treatment location, the number of branch devices required, and/or the size or number of aneurysms to be treated. Deployment of any subsequent branch devices may be realized in a similar manner as described above.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An endoluminal delivery system, comprising:

an introducer sheath having a proximal end, a distal end, a lumen extending between the proximal end and the distal end, and a proximal opening at the proximal end providing access to the lumen;

a delivery catheter configured to be passed through the proximal opening into the lumen of the introducer sheath;

an endoluminal device releasably maintained along the delivery catheter at a delivery profile that is configured for the endoluminal device to be passed through the proximal opening into the lumen of the introducer sheath while the endoluminal device is maintained in the delivery profile, the endoluminal device having an inner lumen, a first opening providing access to the inner lumen, and a second opening providing access to the inner lumen;

a guidewire tube removably received by the endoluminal device such that the guidewire tube is removable from the endoluminal device when the endoluminal device is in the delivery profile, the guidewire tube passing through the first opening of the endoluminal device into the inner lumen of the endoluminal device, and out of the second opening of the endoluminal device, the guidewire tube having a first end, a second end, and a lumen configured to receive a guidewire; and an enlarged feature located between the first end and the second end of the guidewire tube, wherein the first end of the guidewire tube has a first end opening and the second end of the guidewire tube has a second end opening to provide access to the lumen of the guidewire tube and receive the guidewire therethrough, the enlarged feature selectively preventing insertion of the guidewire tube through the proximal opening of the introducer sheath into the lumen of the introducer sheath, and the enlarged feature having a surface texture configured to aid in removal of the guidewire tube from the endoluminal device, the surface texture comprising one or more of: indentations, lines, dimples, or crosshatches.

2. The system of claim 1, wherein the proximal opening into the lumen of the introducer sheath is defined by a hemostatic valve.

3. The system of claim 1, further comprising a guidewire received in the lumen of the guidewire tube.

4. The system of claim 1, further comprising a constraint releasably maintaining the endoluminal device in the delivery profile.

5. The system of claim 1, wherein the enlarged feature includes a portion of the guidewire tube that defines an enlarged outer profile relative to a remaining portion of the guidewire tube.

6. The system of claim 1, wherein the enlarged feature includes at least one of a bead, a ring, a barb, a knob, and a catch.

7. The system of claim 1, wherein the enlarged feature is substantially teardrop shaped.

8. The system of claim 1, wherein the enlarged feature is positioned along a proximal portion of the guidewire tube.

9. The system of claim 1, wherein the enlarged feature defines a maximum diametric dimension that is greater than a maximum diametric dimension of adjacent portions of the guidewire tube by at least 10%, 20%, 30%, 40%, 50%, 60%, 100%, 200%, 300%, or more.

10. The system of claim 1, wherein the enlarged feature is attached around the guidewire tube.

11. An endoluminal delivery system, comprising:

an introducer sheath having a proximal end, a distal end, a lumen extending between the proximal end and the distal end, and a proximal opening at the proximal end providing access to the lumen;

a delivery catheter configured to be passed through the proximal opening into the lumen of the introducer sheath;

an endoluminal device releasably maintained along the delivery catheter at a delivery profile that is configured for the endoluminal device to be passed through the proximal opening into the lumen of the introducer sheath while the endoluminal device is maintained in the delivery profile, the endoluminal device having an inner lumen, a first opening providing access to the inner lumen, and a second opening providing access to the inner lumen;

a guidewire tube removably received by the endoluminal device such that the guidewire tube is removable from the endoluminal device when the endoluminal device is in the delivery profile, the guidewire tube passing through the first opening of the endoluminal device into the inner lumen of the endoluminal device, and out of the second opening of the endoluminal device, the guidewire tube having a first end, a second end, and a lumen configured to receive a guidewire; and an enlarged feature located at the guidewire tube such that a portion of the guidewire tube extends beyond an end of the enlarged feature, wherein the first end of the guidewire tube has a first end opening and the second end of the guidewire tube has a second end opening to provide access to the lumen of the guidewire tube, the enlarged feature selectively preventing insertion of the guidewire tube through the proximal opening of the introducer sheath into the lumen of the introducer sheath, and the enlarged feature having a surface texture configured to aid in removal of the guidewire tube from the endoluminal device, the surface texture comprising one or more of: indentations, lines, dimples, or crosshatches.

12. An endoluminal delivery system, comprising:

an introducer sheath having a proximal end, a distal end, a lumen extending between the proximal end and the distal end, and a proximal opening at the proximal end providing access to the lumen;

a delivery catheter configured to be passed through the proximal opening into the lumen of the introducer sheath;

an endoluminal device releasably maintained along the delivery catheter at a delivery profile that is configured for the endoluminal device to be passed through the proximal opening into the lumen of the introducer sheath while the endoluminal device is maintained in the delivery profile, the endoluminal device having an inner lumen, a first opening providing access to the inner lumen, and a second opening providing access to the inner lumen;

a guidewire tube removably received by the endoluminal device such that the guidewire tube is removable from the endoluminal device when the endoluminal device is in the delivery profile, the guidewire tube passing through the first opening of the endoluminal device into the inner lumen of the endoluminal device, and out of the second opening of the endoluminal device, the guidewire tube having a first end with a first end opening, a second end with a second end opening, and a lumen configured to receive a guidewire; and an enlarged feature located at a position between the first end and the second end of the guidewire tube, wherein the enlarged feature is configured to selectively prevent insertion of the guidewire tube through the proximal opening of the introducer sheath into the lumen of the introducer sheath while the first end opening and the second end opening of the guidewire tube provide access to the lumen of the guidewire tube, and the enlarged feature having a surface texture configured to aid in removal of the guidewire tube from the endoluminal device, the surface texture comprising one or more of: indentations, lines, dimples, or crosshatches.

* * * * *